US010440997B2

(12) United States Patent
Borkovec et al.

(10) Patent No.: US 10,440,997 B2
(45) Date of Patent: Oct. 15, 2019

(54) CAPSULE HAVING A LIQUID TRANSPORTING ELEMENT FOR USES WITH AN ELECTRONIC SMOKING DEVICE

(71) Applicant: FONTEM HOLDINGS 1 B.V., Amsterdam (NL)

(72) Inventors: Vaclav Borkovec, Hamburg (DE); Fiona Collins, Hamburg (DE); Shona Davidson, Cambridge (GB); Andrew Rowbotham, Nottingham (GB)

(73) Assignee: FONTEM HOLDINGS 1 B.V, Amsterdam (NL)

( * ) Notice: Subject to any disclaimer, the term of this patent is extended or adjusted under 35 U.S.C. 154(b) by 0 days.

(21) Appl. No.: 15/519,475

(22) PCT Filed: Oct. 12, 2015

(86) PCT No.: PCT/EP2015/073587
§ 371 (c)(1),
(2) Date: Apr. 14, 2017

(87) PCT Pub. No.: WO2016/059003
PCT Pub. Date: Apr. 21, 2016

(65) Prior Publication Data
US 2017/0231286 A1 Aug. 17, 2017

(30) Foreign Application Priority Data

Oct. 17, 2014 (EP) .................... 14189416

(51) Int. Cl.
*A24F 13/00* (2006.01)
*A24F 17/00* (2006.01)
(Continued)

(52) U.S. Cl.
CPC ....... *A24F 47/008* (2013.01); *A61M 15/0028* (2013.01); *A61M 15/0033* (2014.02);
(Continued)

(58) Field of Classification Search
CPC ..... A24F 47/008; A24F 47/002; B65D 47/36; B65B 3/04; B65B 7/28
(Continued)

(56) References Cited

U.S. PATENT DOCUMENTS 3,721,240 A 3/1973 Tamburri
5,144,962 A 9/1992 Counts et al.
(Continued)

FOREIGN PATENT DOCUMENTS

CA 2641869 A1 5/2010
CN 101228969 A 7/2008
(Continued)

OTHER PUBLICATIONS

European Patent Office, "Extended European Search Report", for EP 14189416.2, dated Jul. 29, 2015, 5 pgs.
(Continued)

*Primary Examiner* — Hae Moon Hyeon
(74) *Attorney, Agent, or Firm* — Perkins Coie LLP; Kenneth H. Ohriner

(57) ABSTRACT

A capsule for use with an electronic smoking device includes a shell (105) having a lateral wall (101, 102) and an end wall (103), wherein the lateral wall (101, 102) and the end wall (103) defines a cavity (110) open at one end (111). A puncturable membrane (104) seals the open end (111) of the cavity (110). A liquid is contained within the cavity (110) by the shell (105) and the puncturable membrane (104), wherein a liquid transporting element (120) is arranged within the cavity (110) enclosed by the puncturable membrane (104) and immersed in the liquid.

15 Claims, 6 Drawing Sheets

Figure 3:
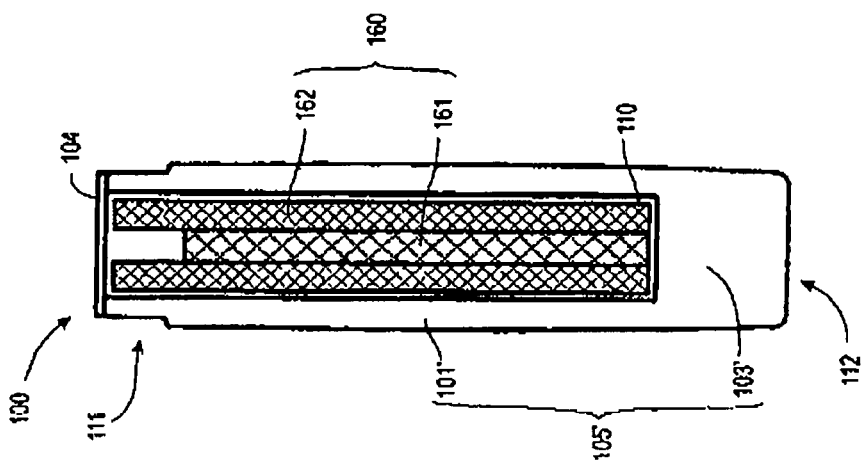

(51) Int. Cl.
| | |
|---|---|
| *A24F 25/00* | (2006.01) |
| *A24F 47/00* | (2006.01) |
| *A61M 15/06* | (2006.01) |
| *A61M 15/00* | (2006.01) |
| *B65B 3/04* | (2006.01) |
| *B65B 7/28* | (2006.01) |
| *B65D 47/36* | (2006.01) |

(52) U.S. Cl.
CPC ............... *A61M 15/06* (2013.01); *B65B 3/04* (2013.01); *B65B 7/28* (2013.01); *B65D 47/36* (2013.01); *A61M 2205/123* (2013.01)

(58) Field of Classification Search
USPC .................................................. 131/329, 328
See application file for complete search history.

(56) References Cited

U.S. PATENT DOCUMENTS

| | | | |
|---|---|---|---|
| 6,715,494 B1 | 4/2004 | McCoy | |
| 8,091,558 B2 | 1/2012 | Martzel | |
| 8,375,957 B2* | 2/2013 | Hon | A24F 47/008 |
| | | | 131/194 |
| 8,678,012 B2* | 3/2014 | Li | A24F 47/008 |
| | | | 128/202.21 |
| 8,813,759 B1 | 8/2014 | Horian | |
| 9,132,248 B2 | 9/2015 | Qui | |
| 2009/0126745 A1 | 5/2009 | Hon | |
| 2009/0272379 A1 | 11/2009 | Thorens et al. | |
| 2010/0200008 A1 | 8/2010 | Taieb | |
| 2010/0308481 A1 | 12/2010 | Oglesby | |
| 2011/0005535 A1 | 1/2011 | Xiu | |
| 2011/0083686 A1* | 4/2011 | Yang | A24D 3/0204 |
| | | | 131/328 |
| 2011/0232654 A1 | 9/2011 | Mass et al. | |
| 2011/0303231 A1* | 12/2011 | Li | A24F 47/008 |
| | | | 131/329 |
| 2012/0199663 A1* | 8/2012 | Qiu | A61M 11/041 |
| | | | 239/8 |
| 2012/0204889 A1 | 8/2012 | Xiu | |
| 2012/0279512 A1 | 11/2012 | Hon | |
| 2013/0096509 A1 | 4/2013 | Avery et al. | |
| 2013/0192615 A1 | 8/2013 | Tucker et al. | |
| 2014/0209108 A1 | 7/2014 | Li et al. | |
| 2014/0261493 A1 | 9/2014 | Smith et al. | |
| 2015/0053220 A1* | 2/2015 | Levy | A24F 47/008 |
| | | | 131/329 |
| 2015/0245669 A1* | 9/2015 | Cadieux | A61M 15/06 |
| | | | 131/329 |
| 2016/0022930 A1* | 1/2016 | Greim | A61M 15/06 |
| | | | 131/328 |
| 2016/0174610 A1* | 6/2016 | Kuczaj | A24F 47/008 |
| | | | 131/328 |
| 2016/0250201 A1* | 9/2016 | Rose | A61K 31/4439 |
| | | | 131/329 |
| 2017/0215485 A1* | 8/2017 | Zitzke | A24F 47/008 |

FOREIGN PATENT DOCUMENTS

| | | |
|---|---|---|
| CN | 201379072 Y | 1/2010 |
| CN | 102160906 A | 8/2011 |
| CN | 202052669 U | 11/2011 |
| CN | 202068930 U | 12/2011 |
| CN | 102379458 A | 3/2012 |
| CN | 202197836 U | 4/2012 |
| DE | 102006041042 A1 | 3/2008 |
| DE | 102007011120 A1 | 9/2008 |
| EP | 2443946 A1 | 4/2012 |
| EP | 2762019 A1 | 8/2014 |
| GB | 2466758 B | 9/2011 |
| JP | 2009537119 A | 10/2009 |
| JP | 201187569 | 5/2011 |
| KR | 101011453 B1 | 1/2011 |
| KR | 20120016167 A | 2/2012 |
| WO | 2009155734 A1 | 12/2009 |
| WO | 2010091593 A1 | 8/2010 |
| WO | 2010145805 A1 | 12/2010 |
| WO | 2011/042212 A1 | 4/2011 |
| WO | 2011131778 A1 | 10/2011 |
| WO | 2013/040193 A2 | 3/2013 |
| WO | 2013040193 A2 | 3/2013 |
| WO | 2013/159245 A1 | 10/2013 |
| WO | WO-2015071703 A1 * | 5/2015 ........... A24F 47/008 |

OTHER PUBLICATIONS

European Patent Office, "International Search Report and Written Opinion", for PCT/EP2015/073587, dated May 3, 2016, 12 pp.
State Intellectual Property Office, Office Action for Chinese Application No. 201580061941.9; dated Jun. 25, 2019; partial English translation; 13 pages.

* cited by examiner

CAPSULE HAVING A LIQUID TRANSPORTING ELEMENT FOR USES WITH AN ELECTRONIC SMOKING DEVICE

TECHNICAL FIELD

The present invention pertains to a capsule for use with an electronic smoking device. The invention further pertains to an electronic smoking device and a method for filling capsules.

BACKGROUND OF THE INVENTION

Electronic smoking devices, e.g. electronic cigarettes, are intended to allow smokers to inhale nicotine or other aerosols of an aromatic liquid without disturbing other persons. An electronic smoking device typically includes an elongated housing which accommodates a reservoir for a liquid and a device for converting the liquid into an aerosol upon activation of the user. The device for converting the liquid into an aerosol is often referred to as atomizer as it atomizes the liquid, i.e. converts the liquid into an aerosol or vapour.

Several approaches have been suggested for electronic smoking devices. One common approach uses a replaceable capsule which includes an elongated shell having an open end and a closed end. The open end of the capsule is sealed with a puncturable membrane to enclose a liquid which contains the compound or compounds to be vaporized. When the capsule is inserted into the smoking device, a puncture element of an atomizer ruptures the membrane and penetrates into the capsule to come into contact with the liquid contained therein. The puncture element is either formed by, or supports, a metal mesh which transports the liquid by capillary action to a heating section of the atomizer. Upon activation of the atomizer, typically by a user's puff, electrical energy powered by a battery is provided to the heating section to vaporize the liquid. The vaporized liquid is transported by the fluid stream caused by the user's puff to a mouth piece at which the user inhales the vaporized liquid. As the vaporized liquid partially condensates into fine droplets at the transport by the fluid stream to form an aerosol, the action of the atomizer is referred to as "atomizing" the liquid into an "aerosol" which is the product of the atomizer.

Electronic smoking devices of this type are often referred to as three-part electronic cigarettes as they include three main parts—the liquid storage tank or capsule, the atomizer, and the control electronics with the battery. An example of such an electronic smoking device is disclosed in EP 2 443 946 A1 which uses an atomizer having a column shaped alloy sponge that pierces a membrane of a liquid storage tank when the liquid storage tank is inserted into the electronic smoking device. The liquid in the liquid storage tank seeps into the sponge of the atomizer, is transported to a heating coil and is vaporized by the heating element.

While the above approach uses a disposable capsule, other approaches combine a liquid storage container and an atomizer into a single unit which is often referred to as "cartomizer". As the liquid storage container is not designed to be disposable, the consumed liquid must be replenished by the user. This type of electronic smoking device is also referred to as two-part cigarette as it includes, as main parts, the cartomizer and the control electronics.

Both approaches provide different benefits and drawbacks for the user. For example, replenishing the cartomizer with a liquid may be difficult and inconvenient for the user as the user needs a syringe or pipette to refill the liquid storage container of the cartomizer.

Using disposable small capsules avoids the need for the user to refill the cartomizer as he can simply replace the empty capsule. However, it has been observed that the liquid is not completely drawn into the atomizer so that a portion of the liquid remains in the capsule. The remaining rest of the liquid is disposed together with the capsule which is disadvantageous from both a commercial and environmental perspective.

In view of the above, it is desired to provide a capsule for use with an electronic smoking device with improved depletion of the liquid.

BRIEF SUMMARY OF THE INVENTION

This object is achieved by a capsule for use with an electronic smoking device according to claim 1 or claim 8. Claim 11 is directed to an electronic smoking device which includes a related capsule. Claim 14 pertains to a method for manufacturing related a capsule.

A capsule for use with an electronic smoking device according to an embodiment includes a shell having a lateral wall and an end wall. The lateral wall and the end wall define a cavity which is open at one end. The other end is closed by the end wall. A puncturable membrane seals the open end of the cavity defined by the end wall and the lateral wall to enclose a liquid contained within the cavity. The capsule further includes a liquid transporting element arranged within the cavity enclosed by the puncturable membrane and immersed in the liquid.

The liquid transporting element contained in the cavity of the capsule facilitates the transport of the liquid to the open end of the cavity when the membrane is ruptured by a rupture element of an atomizer which penetrates into the cavity of the capsule. Upon advancing of the rupture element into the cavity, the liquid transporting element may be pushed towards the closed end of the cavity and ensures that liquid at the closed end comes into contact with the liquid transporting element and can be transported by the liquid transporting element to the rupture element. The rupture element, which typically includes, or is formed by, a metal mesh, a fibrous material, or another micro-meshed material, stays in contact with the liquid transporting element to provide a liquid transporting path from within the cavity to a heating section of the atomizer. By combined action of the rupture element of the atomizer and the liquid transporting element of the capsule, the liquid contained within the cavity of the capsule can be reliably transported to the heating section of the atomizer. Furthermore, as the liquid transporting element is in contact with, or at least extends close to the closed end of the cavity, most of the liquid contained in the cavity is drawn to the heating section by capillary action.

Furthermore, the liquid transporting element provides liquid retaining capabilities to avoid that liquid contained in the cavity leaks or is spilled when the membrane is ruptured. This improves handling of the electronic smoking device and is user-friendly as undesired contact of the liquid with the used is avoided when replacing the capsule.

The liquid transporting element typically includes a plurality of small cavities for improving the liquid transport and the liquid retaining capabilities. For example, the liquid transporting element can be formed of a fibrous material. The fibres of the fibrous material define small cavities and passages between the fibres to provide the liquid transporting element with a large internal surface to improve the liquid transporting properties of the liquid transporting element. Typically, the liquid is transported by capillary action of the small passages and cavities. Capillary action (sometimes capillarity, capillary motion, or wicking) is the ability of a liquid to flow in narrow spaces without the assistance of, and in opposition to, external forces like gravity.

While there are many different materials which can be used for forming the liquid transporting element, special care for selecting a suitable material should be taken. The material should be inert relative to the liquid and have a good wettability for the liquid so that the liquid is drawn into the small passages and cavities of the liquid transporting element.

According to an embodiment, the fibres of the liquid transporting element can include an inorganic material based on, for example, silicon oxide such as silica fibres or amorphous silica fibres such as glass fibres. These materials provide sufficient stiffness, inertness and wettability for liquids. Glass fibres are also less brittle and cheaper than pure silica fibres which make them more attractive for use as material of the liquid transport element. Glass fibres can be made e.g. by adding calcium carbonate to silicon dioxide. Further additives can be added as well.

According to an embodiment, the liquid transporting element can be formed of a porous material which can be shaped to allow easy insertion into the cavity of the capsule. The porous material can be an inorganic material. Alternatively, an organic material having a given stiffness can also be used.

Porous material has a given porosity which is defined by a mean pore size and a pore size distribution. The porosity of the φ can be defined by $$\varphi = \frac{V_V}{V_T}$$

with $V_V$ being the total volume of the pores and $V_T$ the total volume of the porous material (volume of the carrier material and total volume of the pores). Porous material having a so-called open porosity, i.e. interconnected pores, are capable of absorbing liquid or gases while porous material with closed pores cannot uptake another fluid. Real open porous materials typically include closed and interconnected pores. The capability of absorbing a liquid is then determined by the open pores only. The porosity of a material can be experimentally determined, for example, by mercury intrusion porosimetry. Typically, the higher the porosity, the higher is the capacity of the porous material for liquid uptake.

The pore size distribution and the mean pore size influences the capability of the porous material of imbibing liquid as smaller pores, which forms smaller capillaries, typically results in a stronger capillary action than few large pores forming the same total pore volume as the smaller pores.

According to an embodiment, the mean pore size of the material of the liquid transporting element can be between 5 μm and 30 μm, particularly between 5 μm and 15 μm. The mean pore size can be determined using a Scanning Electron Microscope, for example to measure the fibre diameter and then to calculate the mean (arithmetic mean) pore size, i.e. the cross-sectional area of the elongated pores formed between the fibres.

According to an embodiment, the liquid transporting element can have a flexural rigidity, also referred to as flexural stiffness, sufficient for reliable and machine-based handling of the liquid transporting element. Providing the liquid transporting element with a given stiffness facilitates insertion of the liquid transporting element into the cavity in comparison to soft or pliable materials which needs to be stuffed into the cavity. Moreover, automated insertion processes can be envisaged when using a comparably stiff material. The liquid transporting element can therefore be described to be self-supporting.

Fibrous inorganic materials provide sufficient stiffness which can be increased when braiding the fibres, or groups of fibres to a rope or cord.

As explained above, the small passages defined by, and formed between, the individual fibres increase the internal surface of the liquid transporting element. Furthermore, as the passages formed between the fibres have an elongated shape extending in the longitudinal extension of the fibres, the liquid transporting element has an increased transport capability along the fibres.

According to an embodiment, the capsule for use with an electronic smoking device can thus include a shell having a lateral wall and an end wall, wherein the lateral wall and the end wall define a cavity open at one end. A puncturable membrane seals the open end of the cavity defined by the end wall and the lateral wall. A liquid is contained within the cavity by the shell and the puncturable membrane. A liquid transporting element is arranged within the cavity enclosed by the puncturable membrane and immersed in the liquid. The liquid transporting element includes fibres of an inorganic material defining small passages between the fibres for transporting the liquid.

The size, shape and thickness of the individual fibres can vary. For example, fibres of different thickness can be used to form passages of different cross-sections to increase the internal storage capacity of the liquid transporting element while maintaining the transport capabilities. As the differently thick fibres can be randomly distributed, large and small passages or cavities are evenly distributed throughout the liquid transporting element to form a network of interconnected cavities. Providing larger passages and cavities also facilitates uptake of the liquid by and into the liquid transporting element.

According to an embodiment, fibres of substantially the same thickness can be used. The fibre diameter can be, for example, between 5 μm and 25 μm, particularly between 7 μm and 15 μm, and more particularly between 8 μm and 10 μm.

According to an embodiment, the liquid transporting element includes fibres of different thickness to provide passages of different size and thickness as explained above. Mixing fibres of different thickness also allows a finer adaptation of the flexural stiffness of the liquid transporting element by varying the proportion between the thin fibres relative to the thick fibres. For example, the fibre diameter of the thinner fibres can be between 8 μm and 10 μm, and the fibre diameter of the thicker fibres can be larger than 15 μm to have more stiff fibres mixed with less stiff fibres.

The thickness of the fibres can be measured using, for example, a Scanning Electron Microscope. When fibres of substantially the same thickness are used, the thickness distribution of the fibres is mono-modal having a single peak. Different thereto, when using fibres of different thickness, for example of two different thickness ranges, the thickness distribution of the fibres is multi-modal, for example bi-modal having a two distinct peaks.

The thick fibres can also be arranged more centrally than the thin fibres to form a comparably stiff core while the thin fibres surround the stiff core formed by the thick fibres. For example, the thick fibres extend along the liquid transporting element as a bunch of fibres with the thin fibres are braided around the bunch of thick fibres.

To improve the stiffness of the liquid transporting element, groups of fibres each having a plurality of fibres, are braided to form a rope. In addition to that, or alternatively, ring elements can be used to keep the fibres together without tightening them together too strongly.

As the rupture element of the atomizer penetrates into the cavity by a given length, the length of the liquid transporting element can be made shorter than the internal length of the cavity to provide for sufficient space for the rupture element. According to an embodiment, the length of the liquid transporting element in a direction from the end wall of the shell to the puncturable membrane enclosing the open end of the cavity is therefore shorter than the distance from the end wall of the shell to the puncturable membrane. Typically, length of the liquid transporting element is adjusted such that the penetration depth of the rupture element is slightly longer than the space provided by the liquid transporting element to ensure that the rupture element and the liquid transporting elements remains in contact when the rupture element is inserted into the cavity.

According to an embodiment, the length of the liquid transporting element in the direction from the end wall of the shell to the puncturable membrane is shorter than the distance from the end wall of the shell to the puncturable membrane by a distance of, for example, few millimeters. The outer length of the shell can be, for example, between 20 mm to 26 mm. The end wall can have a thickness between about 0.5 mm to about 2 mm. The length of the cavity is then from about 19.5 mm to about 25.5 mm. The penetration depth of the rupture element, when fully inserted into the capsule, can be, for example, in a range of few millimeters so that the above distance is slightly less than the penetration depth.

The fibres of the liquid transporting element can have a diameter between 5 μm and 20 μm, particularly between 8 μm and 10 μm. Fibres of this size are of advantages for silica and glass materials to avoid that the fibres are too stiff and prone to breakage. The actual diameter is not limited to the values given here and can be adapted according to specific needs. Furthermore, other materials may be more advantageously provided with thicker fibres to keep an individual fibre sufficiently stiff but still flexible to some extent.

Each fibre does not need to extend completely from one end to the other end of the liquid transporting element. Fibres of different length can be mixed. The fibres can have a length, for example, of at least 200 μm, for example of at least 300 μm, and particularly of at least 500 μm. The length refers to the arithmetic mean length of the fibres. The length of the fibres can be up to the total length of the cavity, for example up to 2000 μm. The fibres can thus have a length of, for example, between 200 μm and 2000 μm, particularly between 300 μm and 2000 μm, and more particularly between 300 μm and 1500 μm.

The capsule can be used as disposable for an electronic smoking device. The electronic smoking device typically includes an elongated housing having a first hollow part and a second hollow part releasable connected to the first hollow part. The first hollow part and the second hollow part define an internal space of the housing. An electrically heatable atomizer is arranged within the internal space of the housing and includes a rupture element that pierces the membrane of a replaceable capsule when the capsule is removably inserted into the internal space of the housing. Upon insertion of the capsule and connecting the first hollow part to the second hollow part, the rupture element of the atomizer is urged towards the membrane of the capsules and ruptures the membrane upon advancing towards the capsule. The rupture element comes to rest at a given penetration depth where it comes into contact with the liquid transporting element arranged within the capsule. Between the first hollow part and the capsule a sealing member prevents leakage of liquid.

The first hollow part and the second hollow part engage with each other at their respective open ends. The first hollow part forms a mouth piece at its end opposite to its open end. The capsule is insertable into the first hollow part with its closed end pointing towards the mouth piece. The aerosol formed upon activation of the atomizer thus flows through air passages formed between an outer surface of the capsule and an inner surface of the first hollow part to allow an air stream from the atomizer to the mouth piece.

According to an embodiment, a method for filling a capsule includes: feeding an empty capsule from a stock to an insertion apparatus for inserting a liquid transporting element into the empty capsule, wherein the capsule comprises a shell having a lateral wall and an end wall, and wherein the lateral wall and the end wall define a cavity open at one end; feeding a liquid transport element to the insertion apparatus; inserting a liquid transporting element into the cavity of the capsule from the one end of the capsule; filling the cavity of the capsule with a liquid; and sealing the one end of the cavity with a puncturable membrane.

Those skilled in the art will recognise additional features and advantages upon reading the following detailed description, and upon viewing the accompanying drawings.

BRIEF DESCRIPTION OF THE SEVERAL VIEWS OF THE DRAWINGS

The components in the figures are not necessarily to scale, instead emphasis being placed upon illustrating the principles of the invention. Moreover, in the figures, like reference signs designate corresponding parts. In the drawings:

FIG. 1 illustrates a capsule according to an embodiment;

FIG. 2 illustrates a liquid transporting element for a capsule according to an embodiment;

FIG. 3 illustrates a capsule according to a further embodiment;

FIG. 4 shows a REM photograph of a liquid transporting element according to an embodiment;

FIG. 5 shows another REM photograph of the liquid transporting element;

FIG. 6 illustrates an electronic smoking device having a capsule according to an embodiment;

FIGS. 7A and 7B illustrate processes of a method for manufacturing a capsule according to an embodiment; and FIG. 8 is a flow diagram of a series of steps for manufacturing a capsule according to an embodiment.

FIG. 9 is a schematic cross-sectional view of a liquid transporting element used in a capsule.

FIG. 10 is a schematic longitudinal section view of a liquid transporting element used in a capsule.

DETAILED DESCRIPTION OF THE INVENTION

In the following Detailed Description, reference is made to the accompanying drawings, which form a part hereof, and in which are shown by way of illustration specific embodiments in which the invention may be practiced. In this regard, directional terminology, such as "top", "bottom", "front", "back", leading", "trailing", "lateral", "vertical" etc., is used with reference to the orientation of the Figure(s) being described. Because components of embodiments can be positioned in a number of different orientations, the directional terminology is used for purpose of illustration and is in no way limiting. The embodiments being described use specific language, which should not be construed in a limiting sense.

Figure 1:
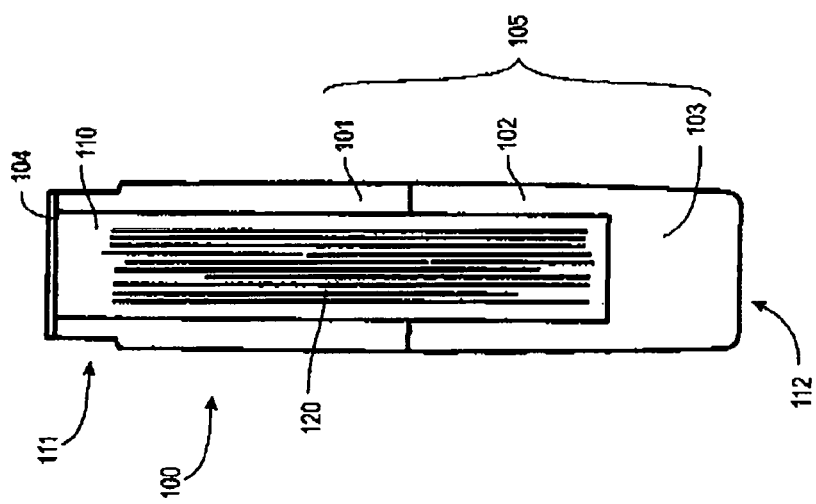

FIG. 1 illustrates a capsule 100 for use with an electronic smoking device according to an embodiment.

The capsule 100 includes a shell 105 formed by a first or front shell part 101 defining a first lateral wall, a second or back shell part 102 defining a second lateral wall 102, and an end wall 103 which is integral with second shell part 102. The first shell part 101 and the second shell part 102 form together a lateral wall of the shell 105 and define together with the end wall 103 a cavity 110 of the capsule 100. The cavity 110 is open at one end 111 and closed at an opposite end 112 by the end wall 103.

The shell 105 of the capsule 100 is illustrated in FIG. 1 as a two-piece element formed by the first shell part 101, which is substantially of hollow-cylindrical shape, and the second shell part 102 which substantially a closed-bottom hollow cylinder. The second lateral wall of the second shell part 102 extends from the end wall 103. The first and second shell parts 101, 102 are connected with each other at their ends facing each other to form a common cavity with a single opened end 111. The shell 105 can also be formed as a single integral part. In this case, the first shell part 101 and the second shell part 102 are integral with each other.

In each case, the shell 105 can be an injection-moulded part made of a hydrophobic material, for example a polyolefin or PTFE such as polypropylene or any other suitable plastic material.

A puncturable membrane 104 covers and seals the open end 111 of the cavity 110 to prevent that a liquid contained within the cavity 110 leaks from the cavity 110. The puncturable membrane 104 can be an aluminium foil which is, for example, heat-sealed to the open end 111 of the cavity 111.

The liquid contained in the cavity 110 typically contains a solvent or carrier for a tobacco compound such as nicotine, a flavour, an ethereal oil, or a mixture thereof. The solvent is typically a hydrophilic and can include constituents like water and polyoles. For example, propylene glycol and/or glycerol can be used which are water-soluble, chemically inert, and non-toxic which renders these compounds attractive as solvent. Typically, the liquid contains water in a range of from 0% to 20% (more preferably of from to 1% to 10%, most preferably of from to 2% to 7%) and polyoles, e.g. glycerol (preferably of from 0% to 90% or even 100%, more preferably of from 10% to 50%, most preferably of from 15% to 25%) and/or propylene glycol (preferably of from 50% to 100%, more preferably of from 60% to 90%, most preferably of from 70% to 80%). All percentages are by weight, related to the total weight of the liquid.

Figure 2:
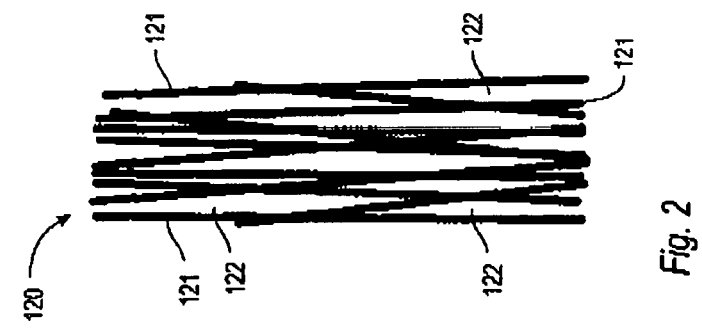

A liquid transporting element 120, which is referred to as wick, is arranged within the cavity 110 enclosed by the puncturable membrane 104 and immersed in the liquid. The wick 120, as best shown in FIG. 2, includes a plurality of individual fibres 121 extending substantially along the longitudinal direction of the wick 120. The individual fibres 121 do not necessarily need to be parallel to each other but may have an orientation slightly deviating from the longitudinal direction, Therefore, when referring to fibres oriented or extending in the longitudinal direction, this orientation also encompasses slight deviations from the strict longitudinal direction. Furthermore, as the fibres 121, or groups of fibres, can be braided, the fibres may be slightly coiled or winded.

The fibres 121 define, and confine, small passages or cavities 122 between the individual fibres 121. The size and shape of the passages 122 may depend on the size of the fibres 121 and the packing density of the fibres 121. As the fibres 121 extend in longitudinal direction, the passages 122 also have a preferred longitudinal extension so that a plurality of longitudinal capillary spaces is formed by the passages 122 in the wick 120.

To provide the wick 120 with a sufficient stiffness, the thickness of the individual fibres 121 can be appropriately selected. For example, the fibres 121 can have a mean thickness of between 5 µm and 20 µm. A specific example is shown in FIG. 3 which is a REM (raster electron microscopy) photograph showing fibres of various thickness in an exemplary range between 8 µm and 10 µm. When describing the wick to include fibres 121 of the same size, this should be construed as referring to the same mean size as the plurality of fibres 121 has a given thickness distribution. The same size means a unimodal thickness distribution, i.e. a distribution with one distinct peak.

In further modifications, fibres 121 having a different thickness can also be used. In this case, the thickness distribution of the fibres 121 corresponds to a bimodal distribution, i.e. a distribution having two distinct peaks. Using a plurality of fibres 121 with a multimodal thickness distribution is also possible.

The thickness of the fibres 121 also depends on the material used for the fibres 121. For stiff materials, such as inorganic materials based on silicon oxide, the fibre thickness is typically in the above mentioned ranged between 5 µm and 20 µm to avoid that the individual fibres 121 become too stiff and may break upon handling. The individual fibres 121 should therefore be sufficiently flexible to allow, for example, braiding or slight twisting or coiling.

When other material are used, such as polymeric materials, the thickness of the individual fibres 121 can be higher as polymeric materials are typically more flexible than inorganic materials. However, the flexibility and stiffness of organic material can be adjusted in a wide range, for example by changing the cross-linking rate or chain size.

To provide the wick 120 with sufficient liquid transporting properties, the individual fibres 121 should not be too thick as thick fibres 121 form larger but less passage 122. As the liquid transport is mainly based on capillary action, a large internal surface formed by the plurality of passages and cavities 122 is desired which is obtainable using comparably thin fibres.

The strength of the capillary action of the liquid transporting element may be quantified as follows: When the liquid transporting element (e.g. such as a wick), is brought in a dry condition into contact with a liquid, it will start absorbing the liquid at a rate which decreases over time. For a bar of material with constant cross-section S that is wetted on one end, the penetration depth of the absorbed liquid along the length of the bar after a time t is $$x=B\sqrt{t},$$

where B is the liquid penetration coefficient [cm s$^{-1/2}$]. The quantity $$m=A\sqrt{t}$$

is the mass of the absorbed liquid with A being the liquid absorption coefficient given in [g/(cm$^2$ h$^{1/2}$)]. B and A are related with each other:

$$B = \frac{A}{\psi \cdot \rho}$$

with $\rho$ the density [g/cm$^3$] of the liquid and $\psi$ the liquid capacity [cm$^3$/cm$^3$] of the porous media. The liquid absorption coefficient A describes the velocity of the mass absorption per unit area. The liquid capacity $\psi$ is closely related with the porosity as it describes the available space for the liquid in the porous media.

The packing density of the fibres 121 can be adjusted by different means. The packing density also influences the size of the cavity and passages 122 and is therefore a further option to tailor the liquid transporting properties.

Figure 4:
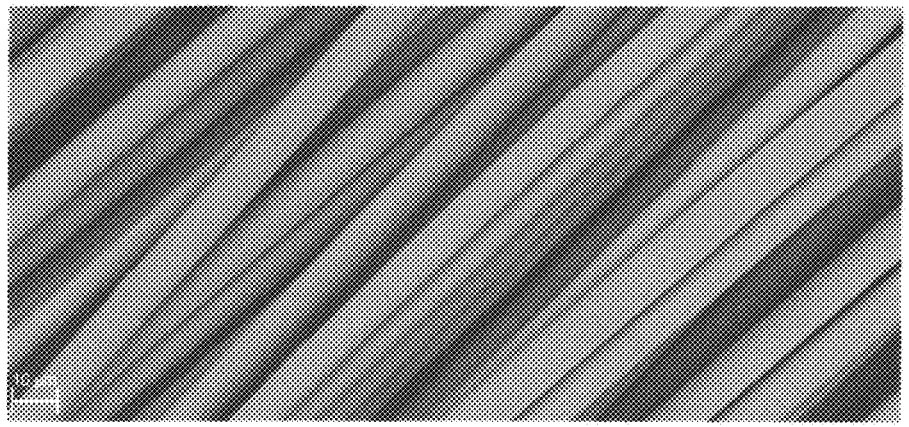

Braiding the fibres 121, or groups of individual fibres 121, also increases the flexural stiffness of the wick 120 and is therefore one option to adjust the overall stiffness of the wick 120. FIG. 4 illustrates a REM photograph of a specific embodiment with groups of fibres 121 being braided to a cord. The numbers of the individual groups of fibres 121, and the number of individual fibres 121 in each group of fibres, can be selected according to specific needs. For example, each group of fibres can include a plurality of fibres forming a strand of the braided cord. The flexural stiffness depends, for example, from the number of individual strands formed by a single group of fibres 121 and the braiding pattern.

Figure 5:

For further tightening the fibres 121 or strands together, ring elements 170 can be used as shown in FIG. 5. Such ring elements 170 can be beneficial at the leading end of the wick 120 to prevent the fibres 121 from fraying and blocking insertion of the wick 120.

The wick 120 is provided with sufficient flexural stiffness to allow automated wick insertion into the cavity 110 of the capsule 100. The upper limit is not specifically of importance in view of the insertion process but should not be too high so that the wick 120 remains sufficient flexible, for example to be coiled on a bobbin or reel.

A specific example of a wick 120 according to an embodiment is made of pure silicon dioxide fibres which are braided or stranded to form a string or cord with a diameter of about 1.5 mm. The fibres 121 are about 8 to 10 μm in diameter. The capillary properties of the material results from the stacking of the fibres 121 which create tiny passages between the fibres 121 to allow the liquid to creep through.

Silicon dioxide fibres have beneficial material properties as this material shows a temperature resistance of up to 1600° C., although such a high temperature resistance is not needed for the wick 120 arranged within the cavity 110 of the capsule 100. The content of silicon dioxide (SiO$_2$) is typically at least 96%. The content of combustible material is preferably equal to or less than 5%.

Silicon dioxide further exhibits a low material loss, when subjected to high temperatures, of about 5% and less and comparably low linear shrinkage properties less than 5%. This material is also beneficial for a wick for use with an atomizer as described further below.

As silicon dioxide fibres are comparably expensive, amorphous silica, e.g. glass, can be used as material for the fibres 121. Glass is a cheaper and less brittle than pure silica. Glass can be made by adding calcium carbonate to the silicon dioxide, as well as other additives if desired. Addition of calcium carbonate results in a cheaper product with a lower melting point, which is, however, not critical for the intended application as wick material for the capsule.

An alternative material is polyester for the fibres 121. To provide the polyester fibres with sufficient flexural stiffness, the thickness of each fibre 121 should be selected accordingly. Polyester is less expensive in comparison to silicon dioxide and easy to handle as this material is less brittle.

Wicks which are too soft are not suitable for automated insertion processes as the wick will be pressed to some degree. Soft materials such as polyester sponges or cotton-like fibrous materials may be compressed which can affect the capillary properties of the material. Another disadvantage of sponge-like wicks is that the absorption of the liquid into the sponge is very time consuming and does not allow for a fast filling of the capsule at high speed which is intended for an automated process. When using sponges, the liquid needs a certain time to be soaked by the sponge before more liquid can be added. This requires a step-wise filling of the cavity with liquid which is time consuming.

Another beneficial material for the wick includes a porous material forming a cylindrical structure which has a hollow section to allow insertion of a filling needle for filling the cavity. FIG. 3 illustrates an embodiment of a capsule 100 having a wick 160, which forms in this embodiment the liquid transporting element, comprised of porous material. In addition to the different wick, the embodiment of FIG. 3 differs from the embodiment of FIG. 1 in that the shell 105' is a single integrally formed body having a lateral wall 101' integral with an end wall 103'.

The wick 160 can have a size and shape adapted to nearly completely fill the cavity 110 of the capsule 100. As illustrated in FIG. 3, the wick 160 can include a centre portion 161 and an outer portion 162 surrounding the centre portion 161. The porous material of the centre portion 161 can have a mean pore size which is lower than the mean pore size of the outer portion 162 to provide the wick 160 with a non-uniform porosity distribution. For example, the porosity can be adjusted such that the absorptive capacity increases radially from the centre of the cylinder to the outer periphery.

The centre portion 161 is recessed relative to the outer portion 162 at the end of the wick 160 facing the puncturable membrane 104 to form the hollow section for the needle to be inserted to facilitate rapid automated needle filling of the cavity 110. Due to the different porosity, a larger total cavity volume is provided to increase the storage capacity within the wick 180. A higher porosity of the centre portion 161 also increases the uptake capacity of the liquid during filling which is beneficial for automated filling.

The porous material can be comparably stiff which makes the insertion process easier as a stiff material is also dimensionally stable. Furthermore, different to a fibrous wick, the wick 160 made of one or two porous materials do not fray at its ends so that the outer size and shape of the wick 160 can substantially correspond to the internal space of the cavity 110 as the ends are not expanded by fraying. In comparison to a fibrous wick, the volume of the porous wick 160 can thus be increased to improve the capillary efficiency.

Figure 9:
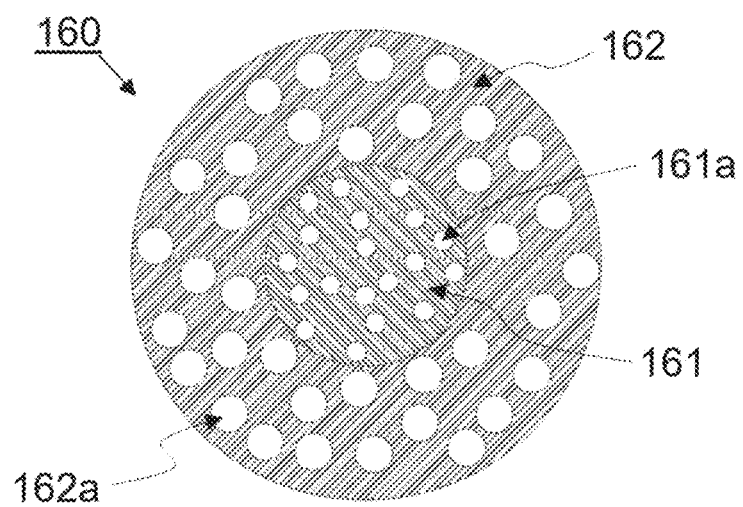

Furthermore, using porous materials of different porosity for the centre portion 161 and the outer portion 162 allows tailoring of the capillary function to ensure that the capillary action remains substantially constant until the liquid in the cavity 110 is depleted. For example, as illustrated in FIG. 9, the centre portion 161 can have smaller pores 161a with increased capillary action in comparison to the outer portion 162 having larger pores 162a. The outer portion 162 thus functions as reservoir while the centre portion 161 functions as transport zone absorbing or sucking the liquid contained in the outer portion 162. The liquid is therefore completely drawn into the centre portion 161 which increases the depletion rate of the capsule 100.

Figure 10:
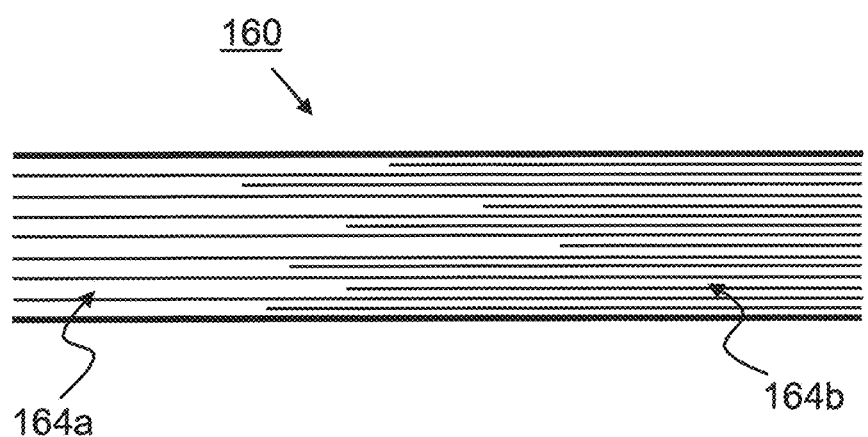

According to a further embodiment, the porous material can have a non-uniform pore size distribution that changes in the axial or longitudinal axis of the porous material, as illustrated in FIG. 10. For example, small pores 164a can be at the end facing the membrane (sealing foil end), while large pores 164b are at the end facing the bottom of the capsule (capsule bottom end). The axial inhomogeneous pore size distribution improves suction and thus transport in axial direction which allows to completely nearly empty the cavity as also liquid, which is at the capsule bottom end of the porous material is transported.

According to an embodiment, the porous material can have a non-uniform porosity distribution both in axial direction and in radial direction. This would encourage liquid to travel from the outside of the porous material to the centre of the porous material, and from the capsule bottom end of the porous material to the sealing foil end.

FIGS. 4 and 5 are REM photographs of a liquid transporting element in accordance with an embodiment of the present invention.

In the example shown, illustrated in the Figures the liquid transporting element comprises a wick which is made of pure silicon dioxide fibres which are splined to form a string with diameter 1.5 mm. The fibres are around 8-10 microns in diameter. The capillary properties of the material are given from the stacking of the fibres that create tiny passages for the liquid to creep through.

As can be seen in the FIGS. 4 and 5, the arrangement of the individual fibres is such that the passages between the fibres are substantially aligned with the longitudinal extent of the wick 160. When arranged within a capsule, the passages between the fibres are also similarly aligned with the longitudinal extent of the capsule 100 which facilitates liquid being drawn from the end of the cavity 110 within the capsule 100 remote from an open end of the capsule 100.

An electronic smoking device 200 according to an embodiment is described with reference to FIG. 6. The smoking device 200 includes an elongated housing 210 comprising a first hollow part 211 and a second hollow part 212 releasably connected to the first hollow part 211. The first hollow part 211 and the second hollow part 212 define together an internal space 220 of the housing 210. Each of the first and second hollow parts 211, 212 is basically cylindrically shaped and has a closed end and an open end.

Figure 6:
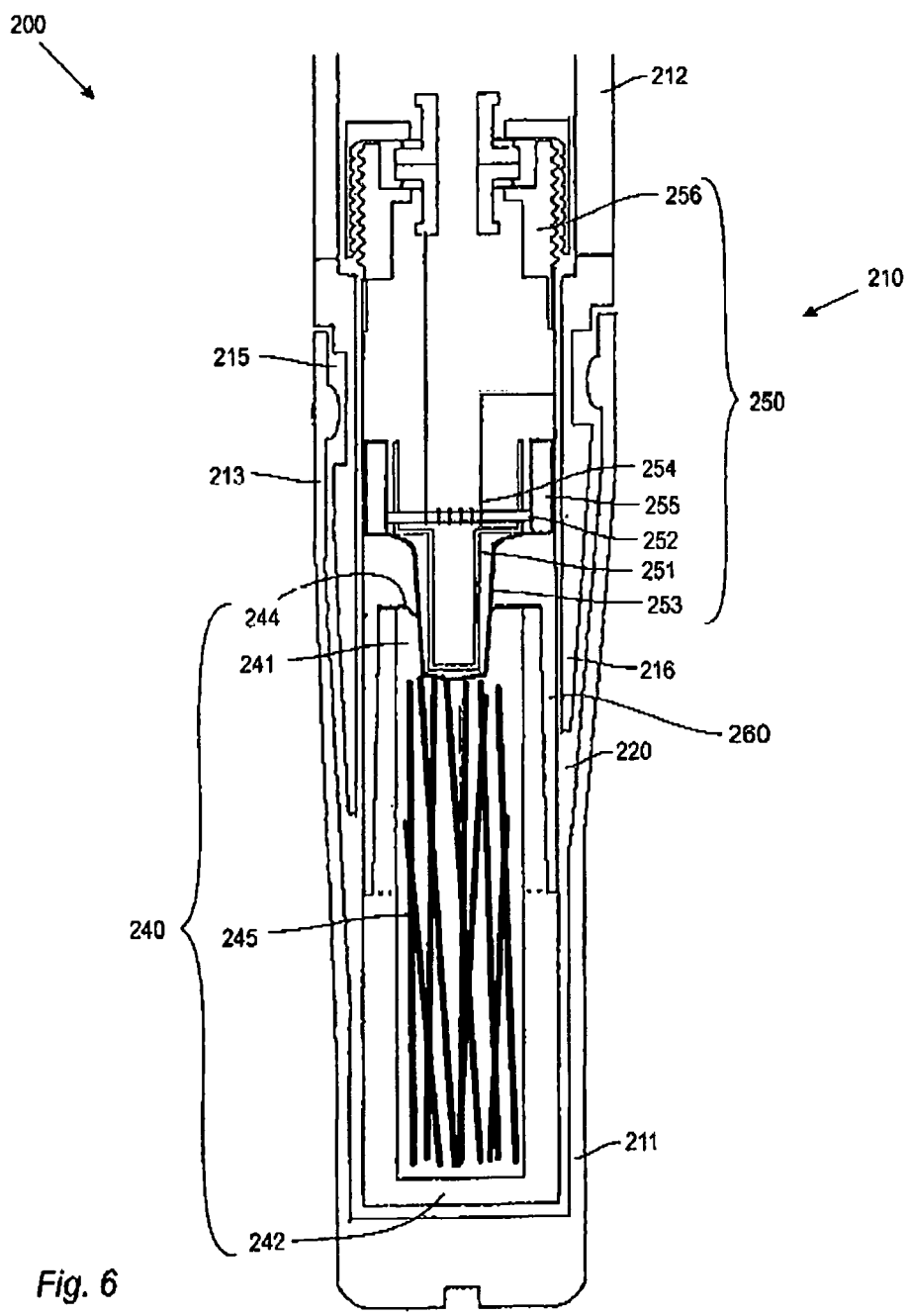

As illustrated in FIG. 6, the first hollow part 211 and the second hollow part 212 engage with each other at their respective open ends for example by means of a snap fit. For example, the first hollow part 211 can be provided with deflectable arms 213 each having a nose 214 projecting radially inwardly to engage with a recess 215 formed at the outer side of the second hollow part 212. When the first and second hollow parts 211, 212 are pushed with their opens ends towards each other, the arms 213 come into contact with a conically shaped open end 216 of the second hollow part 212 and are radially deflected until the noses 214 snap back into the recesses 215 provided at the second hollow part 212. Other releasable connections between the first and second hollow part 211, 212 are also possible and include, for example, threw connections and bayonet connections.

The first hollow part 211 forms a mouth piece at its closed end opposite to its open end at which the user sucks on the electronic smoking device 200 to generate an underpressure or air stream within the internal space 220 of the housing 210. A capsule 240 is insertable into the first hollow part 211 with the closed end 242 of the capsule 240 pointing towards the mouth piece of the housing 210.

An atomizer 250 is accommodated and fixed in the second hollow part 212. The atomizer 250 includes a rupture element which includes an atomizer bridge 251 and a nickel foam or nickel mesh 253 surrounding and supported by the bridge 251. The bridge 251 can be formed by a sufficiently rigid metal wire bracket to allow rupture of the puncturable membrane 244 of the capsule 240 as described further below.

The atomizer 250 further includes a cylindrical nickel foam part 255 (or cylindrical nickel mesh part) which is in contact with the nickel foam 253 supported by the bridge 215251. The cylindrical nickel foam part 255 and the nickel foam 253 form together a liquid transporting path of the atomizer 250 to transport the liquid from a cavity 241 of the capsule 240 to a glass fibre wick 252 of the atomizer 250 around which a heating coil 254 is wound. The heating coil 254 is connected to a battery and control circuitry which are not shown in FIG. 6. The battery and the control circuitry are accommodated in the second hollow part 212 of the housing 210.

When the capsule 240 is inserted into the first hollow part 211 with the open end sealed by the membrane 244 facing the atomizer, the bridge 251 pierces and ruptures the membrane 244 with a not-illustrated piercing spike formed at the leading end of the bridge 251. Upon further pushing the first and the second hollow parts 211, 212 toward each other, the nickel foam 253 supported by the bridge 251 enters the interior of the cavity 241 of the capsule 240 and comes into contact with a wick 245 arranged within the cavity 241 of the capsule 240 to form a liquid transporting path from within the cavity to the glass fibre wick 252.

The bridge 251 advances into the cavity 241 by given extent which depends on the length of the bridge 251 and the final arrangement of the capsule 240 and bridge 251 relative to each other when the first and the second hollow parts 211, 212 fully engages with each other.

Typically, the wick 245 accommodated within the cavity 241 is cut to a length which ensures sufficient contact with the bridge 251 without generating a large tension for the wick 245 and the bridge 251. For example, if the bridge 251 enters the capsule 240 by a length of 3 mm, the wick 240 is cut to the length of the cavity 241 minus 3 mm. The wick 245 is thus shorter than the length of cavity 241 of the capsule 240.

A wick length shorter than the length of the cavity 241 furthermore ensures a proper sealing of the cavity 241 by the membrane 244, since the injection of the liquid during the filling process can cause the wick 245 to rise out of the capsule if the material of the wick 245 does not absorb the liquid fast enough. This will be explained in more detail with reference to the manufacturing processes further below.

Since the cavity 241 of the capsule 240 has typically a comparably small volume, the surface tension of the liquid contained in the small and narrow cavity 241 acts against withdrawal of the liquid from the cavity. This may effectively limit the transfer of liquid to the glass fibre wick 252 if no additional means are provided. For example, when a capsule without wick is pierced onto the bridge of the atomiser 250, the nickel foam 253 absorbs the liquid via capillary action. The level of the liquid within the capsule will therefore decrease during consumption of the liquid. When the level of liquid decreases so that the liquid is no longer in contact with the nickel foam 253 supported by the bridge 251, the capillary 'connection' is lost, and the liquid remains inside the capsule, and there is an under supply of liquid to the atomizer.

Complete depletion of the liquid is ensured when using a wick 245 accommodated in the capsule 240, as the wick 245, when the capsule 240 is inserted into the housing 210, transports the liquid from the bottom of the cavity 241 toward the nickel foam 253 and thus provides a substantially constant capillary flow until the liquid is completely depleted. Hence, the consumption efficiency is increased, and significant less liquid is disposed.

Figure 7A:
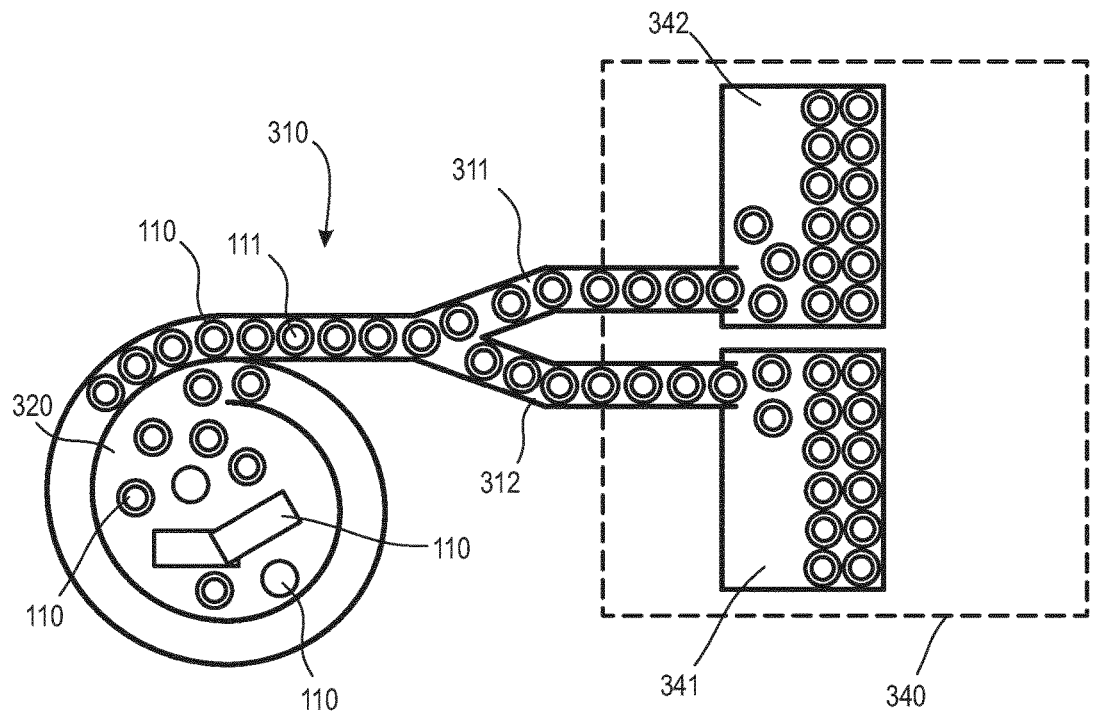

A process for manufacturing a capsule according to an embodiment is described with reference to FIGS. 7A, 7B and 8.

The wick can be manufactured, for example, by braiding multiple strands each including a plurality of individual fibres, for example glass fibres or silica fibres, into a long cord. The cord is wound onto a large bobbin and then placed onto a cutting machine which draws the cord and cuts it size using a rotary cutting saw to obtain individual wicks. The stiff and robust nature of the wick allows an automated wick insertion process as described further below.

An insertion system adapted to allow automated insertion of the wick can be based on a pallet transfer unit where the capsules are first sorted followed by insertion of the wicks. A pallet transfer unit can include a dead plate with aluminium pallets being pushed around this plate. The pallets are moved around several working areas and will finally be transferred into a carrier for shipment.

Several processes are described subsequently.

Process 1 (410)

For inserting the wicks into capsules, the capsules are first sorted and oriented properly. For example, the capsules 100 can be fed by a vibratory bowl feeder 310 as illustrated in FIG. 7A. The vibratory bowl feeder 310 includes a vibrating bowl 320 with a spiral-shaped ramp along which the capsules 100 move due to the vibration of the bowl 320. As the capsules 100 have an asymmetrical shape with a barycentre located closer to the end wall 103, the initially randomly orientated capsules 100 orientate with their open end 111 facing upwards when subjected to vibration and movement along the spiral-shaped ramp. The open ends 111 are illustrated in FIG. 7A.

The vibratory bowl feeder 310 further includes two feeder lanes 311, 312 which branches-off from each other to transport the capsules 100 to two pockets 341, 342 of a pallet 340 at a loading station. Each pallet 340 can include multiple pockets 341, 342 depending on circumstances. The pallet 340 will be manipulated underneath the feeder lanes 311, 312, and pairs of pockets 341, 342 of the pallet 340 are filled within a given operating time.

Process 2 (420)

In a further process, the pallet 340 is moved to an inspection station (not shown) for checking whether the capsules 100 have been correctly placed into the pockets 341, 342 of the pallet 340. Pockets 341, 342 with misaligned capsules 100 or damaged capsules 100 will be rejected.

Process 3 (430)

Figure 7B:
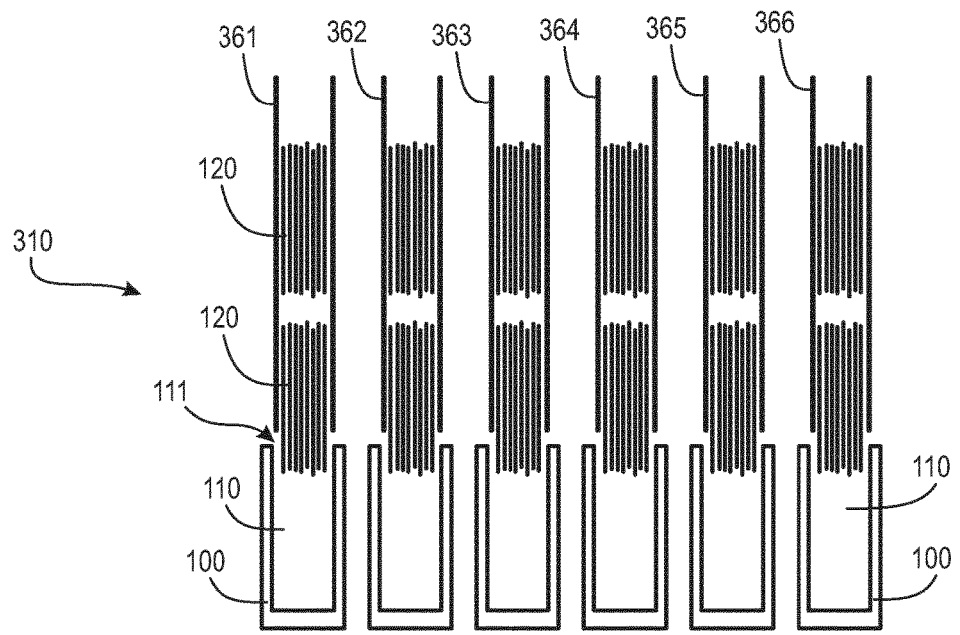
Figure 8:
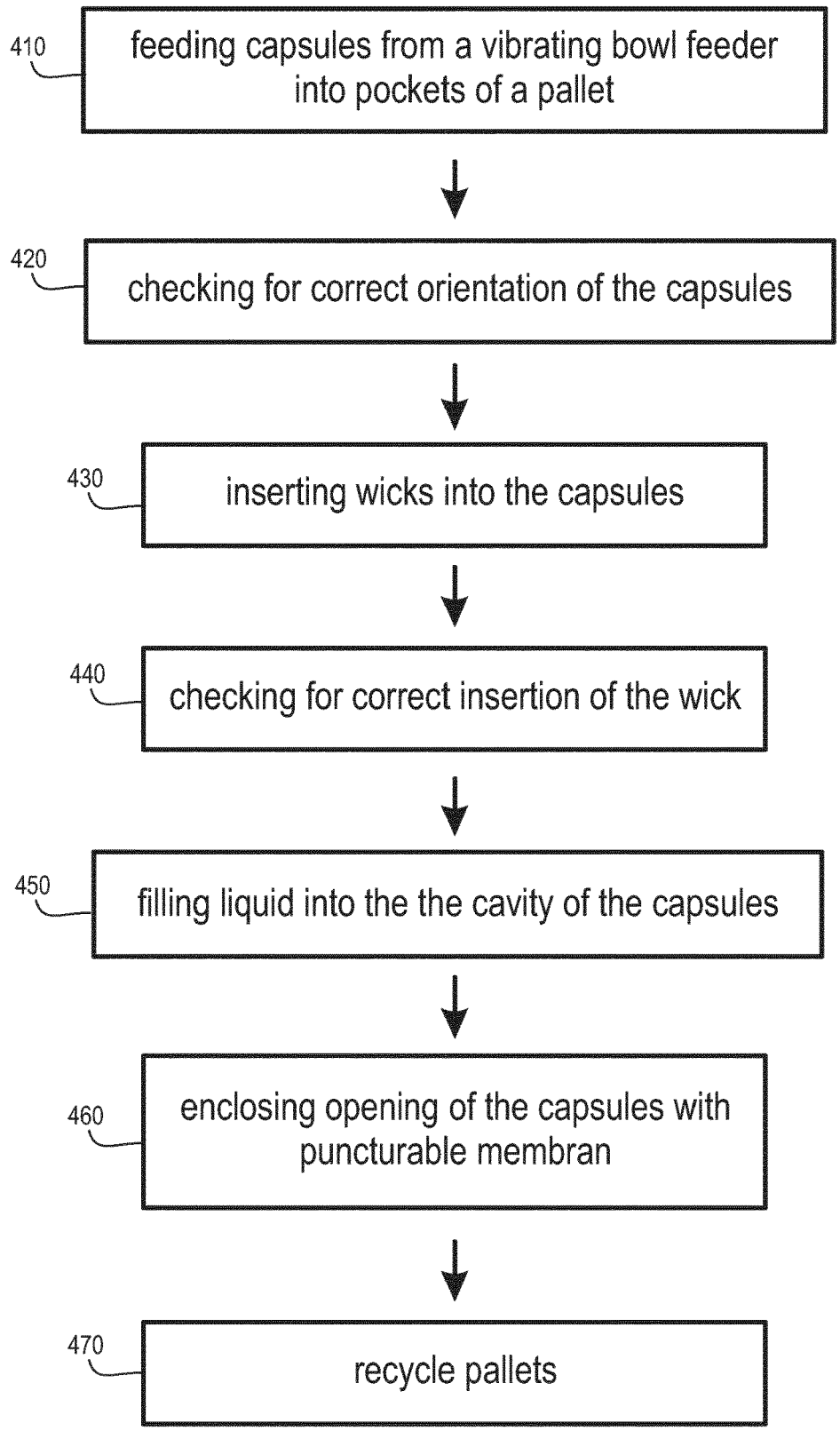

If a row of capsules 100, for example 6 capsules if each pocket 341, 342 is sized to accommodate rows of 6 capsules, is deemed to be correctly oriented and not damaged, the pocket 341, 342 is transferred to six-lane wick feeding station 360 as indicated in FIG. 7B. The feeding station 360 includes a number of wick feedings lanes 361 to 366. The number of the wick feeding lanes 361 to 366 corresponds to the numbers of capsules 100 in a row of a pocket 341, 342.

As illustrated in FIG. 7B, the open ends of the feedings lines 361 to 362 are close to the open ends 111 of the capsules 100 so that the wicks 120 fed by the feeding lines 361 to 366 pushes the wicks 120 into the cavity 110 of the capsules 100.

Process 4 (440)

After insertion of the wicks 120, the pallets 340 are moved to an inspection station for inspection whether the wicks 120 have been completely and correctly inserted into the capsules 100 and that none of the wicks 120 is either hanging over the open end 111 the capsule 100 or has fallen out and is lying on the pallet 340. Inspection can be done automatically using a camera and image-processing software. If any there is any misplacement of a wick 120 detected, the complete row the capsules is rejected into a reject chute which transports the capsules 100 to a waste bin.

As the complete row is rejected when misplaced wick 120 is detected, the number of capsules 100 within one row should not be too high.

The pallets 340 which pass inspection can either be emptied with the capsules 100 collected in a separate carrier or transferred to a liquid filling section.

Process 5 (450)

In a further process, the liquid containing the tobacco compound is filled into the cavities 110 of the capsules 100, for example by inserting a needle into the cavity 110. As the wick 120 is shorter than the internal length of the cavity 110, the needle can be inserted to a given extent without pressing and damaging the inserted wick 120.

The needle may also remain in the cavity 110 until the wick 120 is completely soaked with the liquid. This ensures that the wick 120 is not pushed out of the cavity 110 during the filling process due to air entrapped in the passages which needs a given time to be replaced by the liquid.

Process 6 (460)

After filling the capsules 100 with liquid, the open end 111 is sealed by the pun arable membrane 104 as illustrated in FIG. 1, for example. The sealed capsules 100 are then removed from the pallets, packed and shipped.

Process 7 (470)

After removing the capsules 100 from the pallets 340, the pallets 340 are cleaned with, for example, vacuum to remove any particle from the pallets 340 and the pockets 341, 342, and then allowed to recycle to the loading stations.

The above processes can be carried out at a single wick inserting and filling system. Alternatively, the wick insertion process can be handled by a wick insertion apparatus separate to a liquid filling apparatus. In this case, sealing of the capsules 100 with the puncturable membrane 104 will be conducted by the liquid filling apparatus.

The invention claimed is:

1. A capsule for use with an electronic smoking device, the capsule comprising:
   a shell having a lateral wall and an end wall, the lateral wall and the end wall defining a cavity open at one end;
   a puncturable membrane sealing the open end of the cavity defined by the end wall and the lateral wall;
   a liquid contained within the cavity by the shell and the puncturable membrane; and
   a liquid transporting element arranged within the cavity enclosed by the puncturable membrane and immersed in the liquid, the liquid transporting element comprising fibres of an inorganic material defining passages between the fibres for transporting the liquid.

2. The capsule according to claim 1, wherein the liquid transporting element comprises fibres of different thickness.

3. The capsule according to claim 1, wherein the fibres are provided in groups and the groups of fibres are braided to form a rope.

4. The capsule according to claim 1, wherein the cavity has a longitudinal axis and the fibres are substantially oriented in a direction parallel to the longitudinal axis.

5. The capsule according to claim 1, wherein the fibres of the liquid transporting element comprise an inorganic material based on silicon oxide.

6. The capsule according to claim 1, wherein the fibres of the liquid transporting element comprise a glass material.

7. The capsule according to claim 1, wherein a length of the liquid transporting element in a direction from the end wall of the shell to the puncturable membrane enclosing the open end of the cavity is shorter than the distance from the end wall of the shell to the puncturable membrane.

8. The capsule of claim 1 with the liquid transporting element having a center portion with first pores having a first pore size, the center portion being surrounded by an outer portion with second pores having a second pore size different from the first pore size.

9. The capsule of claim 1 with the liquid transporting element having an axially inhomogeneous pore size distribution.

10. The capsule of claim 1 with the liquid transporting element having a radially inhomogeneous pore size distribution.

11. A capsule for use with an electronic smoking device, the capsule comprising:
    a shell having a lateral wall and an end wall, the lateral wall and the end wall defining a cavity open at one end;
    a puncturable membrane sealing the open of the cavity defined by the end wall and the lateral wall;
    a liquid contained within the cavity by the shell and the puncturable membrane; and
    a self-supporting liquid transporting element arranged within the cavity enclosed by the puncturable membrane and immersed in the liquid.

12. An electronic smoking device, comprising:
    an elongated housing comprising a first hollow part and a second hollow part releasably connected to the first hollow part, the first hollow part and the second hollow part defining an internal space of the housing;
    a replaceable capsule removably inserted into the internal space of the housing, the replaceable capsule including a shell having a lateral wall and an end wall, the lateral wall and the end wall defining a cavity open at one end, a puncturable membrane sealing the open end of the cavity, a liquid contained within the cavity by the shell and the puncturable membrane, and a liquid transporting element immersed in the liquid, the liquid transporting element comprising fibres of an inorganic material defining passages between the fibres for transporting the liquid;
    an electrically heatable atomizer within the internal space of the housing, the atomizer comprising a rupture element extending into the open end of the cavity of the capsule through a rupture of the puncturable membrane of the capsule when the capsule is inserted into the internal space, wherein the rupture element comes into fluid contact with the liquid transporting element of the capsule.

13. The electronic smoking device according to claim 12, wherein the first hollow part has a closed first end and an open second end, and the second hollow part has a first end and a second end, with the open second end of the first hollow part engaged with the first end of the second hollow part, and the second end of the second hollow part forms a mouth piece wherein the capsule is insertable into the first hollow part with the puncturable membrane adjacent to the atomizer.

14. The electronic smoking device according to claim 13, wherein an air passage is formed between an outer surface of the capsule and an inner surface of the first hollow part to allow an air stream from the atomizer to the mouth piece.

15. A method for filling a capsule, comprising:
    feeding an empty capsule from a stock to an insertion apparatus wherein the capsule comprises a shell having a lateral wall and an end wall, the lateral wall and the end wall defining a cavity open at one end;
    feeding a liquid transporting element to the insertion apparatus;
    inserting the liquid transporting element into the cavity of the capsule from the one end of the capsule;
    filling the cavity of the capsule with a liquid; and
    sealing the one end of the cavity with a puncturable membrane.

* * * * *